(12) United States Patent
Roninson et al.

(10) Patent No.: US 10,584,369 B2
(45) Date of Patent: Mar. 10, 2020

(54) CELL-BASED METHODS FOR MEASURING ACTIVITY OF A PROTEIN INHIBITOR

(71) Applicant: Senex Biotechnology, Inc., Columbia, SC (US)

(72) Inventors: Igor B Roninson, Lexington, SC (US); Donald C Porter, Columbia, SC (US); Serena Altilia, Columbia, SC (US)

(73) Assignee: Senex Biotechnology, Inc., Columbia, SC (US)

( * ) Notice: Subject to any disclaimer, the term of this patent is extended or adjusted under 35 U.S.C. 154(b) by 449 days.

(21) Appl. No.: 14/153,383

(22) Filed: Jan. 13, 2014

(65) Prior Publication Data
US 2014/0199708 A1    Jul. 17, 2014

Related U.S. Application Data

(60) Provisional application No. 61/751,385, filed on Jan. 11, 2013.

(51) Int. Cl.
| | | |
|---|---|---|
| *C12N 9/12* | (2006.01) | |
| *C12Q 1/48* | (2006.01) | |
| *G01N 33/573* | (2006.01) | |
| *G01N 33/50* | (2006.01) | |

(52) U.S. Cl.
CPC ......... *C12Q 1/485* (2013.01); *G01N 33/5008* (2013.01); *G01N 33/573* (2013.01)

(58) Field of Classification Search
CPC ....................................................... C12Q 1/48
See application file for complete search history.

(56) References Cited

U.S. PATENT DOCUMENTS

2004/0018529 A1*  1/2004  Li ...................... C12N 15/1034
                                                                506/10

FOREIGN PATENT DOCUMENTS

| WO | WO2007133772 | * | 11/2007 | ............. | A61K 31/44 |
| WO | WO2009/036016 | * | 3/2009 | ............. | A01N 43/40 |

OTHER PUBLICATIONS

Winter et al, Caspase-1 Enhances the Apoptotic Response of Prostate Cancer Cells to Ionizing Radiation. Anticancer Research 24: 1377-1386 (2004).*
Braun et al, Investigation of the cell cycle regulation of cdk3-associated kinase activity and the role of cdk3 in proliferation and transformation. Oncogene. Oct. 29, 1998;17(17):2259-69.*
Shockett et al, Inducible Gene Expression Using an Autoregulatory, Tetracycline-Controlled System In: Current Protocols in Molecular Biology (2002) John Wiley & Sons, Inc. Unit 16.14.*
Braun et al, Deregulated expression of CDK2- or CDK3-associated kinase activities enhances c-Myc-induced apoptosis. DNA Cell Biol. Sep. 1998;17(9):789-98.*
Malumbres, Cyclin-dependent kinases. Genome Biology 2014, 15:122.*
Chen et al, Design, Synthesis, and Biological Evaluation of Isoquinoline-1,3,4-trione Derivatives as Potent Caspase-3 Inhibitors. J. Med. Chem. 2006, 49, 1613-1623.*
Crawford et al, Targeting Bcl-2 in Herceptin-Resistant Breast Cancer Cell Lines. Curr Pharmacogenomics Person Med. Sep. 2011 ; 9(3): 184-190.*
Uhlmann et al, A Potent Cell Death Activity Associated with Transient High Level Expression of BCL-2. J Biol Chem vol. 273, No. 28, Issue of Jul. 10, pp. 17926-17932, 1998.*
Sharma et al, Cyclin dependent kinase 5 (Cdk5) mediated inhibition of the MAP kinase pathway results in CREB down regulation and apoptosis in PC12 cells. Biochemical and Biophysical Research Communications 358 (2007) 379-384.*
Muruais et al, The Cdk5 Inhibitor Roscovitine Strongly Inhibits Glucose Uptake in 3T3-L1 Adipocytes Without Altering GLUT4 Translocation From Internal Pools to the Cell Surface. J. Cell. Physiol. 220: 238-244, 2009.*
Muller et al, Efficient Transfection and Expression of Heterologous Genes in PC12 Cells. DNA and Cell Biology vol. 9, No. 3, 1990 p. 221-229.*
Meikrantz et al, Suppression of Apoptosis by Dominant Negative Mutants of Cyclin-dependent Protein Kinases. J Biol Chem vol. 271, No. 17, Issue of Apr. 26, pp. 10205-10209.*
Luo et al, Application of the Fluorescence Resonance Energy Transfer Method for Studying the Dynamics of Caspase-3 Activation during UV-Induced Apoptosis in Living HeLa Cells. BBRC 283, 1054-1060 (2001).*

\* cited by examiner

*Primary Examiner* — Sheridan Swope
(74) *Attorney, Agent, or Firm* — Quarles & Brady LLP

(57) ABSTRACT

The invention provides a method for determining the activity of an inhibitor of a target protein that has a deleterious effect on cell growth. The principle of the claimed method is that a compound that inhibits the function of an overexpressed protein will relieve the detrimental effect of such overexpression in a concentration-dependent manner, thereby allowing the determination of the activity of the compound in inhibiting its target protein in live cells.

13 Claims, 5 Drawing Sheets

A

WT CDK3

B

E195D CDK3

CELL-BASED METHODS FOR MEASURING ACTIVITY OF A PROTEIN INHIBITOR

STATEMENT OF GOVERNMENT SUPPORT

This invention was supported in part by NIH grant R44 CA141845. The government has certain rights in this invention.

BACKGROUND OF THE INVENTION

Field of the Invention

The invention relates to the measurement of activity of protein inhibitors.

Summary of the Related Art

Potent and selective inhibitors of enzymes and other bioactive proteins are used for numerous medical and biotechnological applications, as well as for research. The potency of a protein inhibitor is usually measured in cell-free assays, using purified protein preparations. The selectivity of the inhibitor is typically deduced by comparing its activities for the inhibition of different proteins. It is well known in the art, however, that the inhibitory activity of a compound, which is usually expressed as IC50 (the concentration required for half-maximal protein activity inhibition) or Ki (the measure of bond-tightness between the enzyme and its inhibitor) may vary depending on many factors. In the case of enzyme inhibitors, these factors may include (i) the nature of enzyme preparation (for example, what type of cells the recombinant protein was expressed in), (ii) the quality of the enzyme preparation, (iii) the nature and the quality of additional subunits of a multi-subunit enzyme, (iv) the nature and quality of the substrate used in the enzymatic reaction, (v) the buffer composition and temperature conditions of the reaction, and other variable factors.

As a recent example, Echalier et al. (Chemistry & Biology 19, 1028-1040, 2012) show that Ki values for cyclin-dependent kinase (CDK) inhibitors, were different when the CDKs were combined with different regulatory cyclin proteins. On the other hand, U.S. Provisional Application No. 61/734,127 teaches that both the Km values for ATP (used in the assays for IC50 determination) and the relative activity of a CDK inhibitor, Purvalanol A, for CDK2 and CDK3 kinases were different from the values reported by Echalier et al., in the assays conducted using different enzyme preparations, phosphorylation substrates and ATP concentrations.

The utility of a protein inhibitor lies in its effect on the target protein within a cell rather than in an artificial cell-free assay. Therefore the most pertinent inhibitory activity is the one measured in a cell-based assay, which measures directly the effect of the inhibitor on the activity of the target protein in an intact cell. However, direct cell-based assays are available for only a small fraction of protein targets. The most widely used class of such assays is aimed at cell surface receptors of specific ligands, where the activity of a receptor's antagonist is measured by the competition for receptor-specific ligand binding at the cell surface. Another general class of cell-based assays is based on the use of promoter-reporter constructs where the promoter activity is dependent on the binding of a specific transcription factor to its binding site in a promoter. The ability of a compound to inhibit the transcription factor activity within the cell can be measured by its effect on the reporter expression from the promoter (In the latter case, however, the inhibition of promoter activity may also reflect an indirect effect on the transcription factor.)

For most of the intracellular proteins, however, target-specific cell-based assays are not available. For example, a cell-based assay for a specific protein kinase could measure the phosphorylation of an intracellular protein substrate, provided that the substrate is phosphorylated only by the target kinase. However, there are very few, if any, examples of a protein being phosphorylated by only a single kinase. Hence, there is great need in the art for a different type of cell-based assays specific for a particular protein.

BRIEF SUMMARY OF THE INVENTION

The instant invention provides a novel type of specific cell-based assays suitable for many protein targets. Since many proteins have significant effects on cell physiology, the expression of such proteins at a very high supra-physiological level is likely to be detrimental to cell homeostasis and therefore would inhibit cell growth. The issue of cell toxicity of overexpressed proteins is often considered in the area of recombinant protein production, as it presents an obstacle to obtaining a high protein yield. These issues have been discussed for both bacterial (Saida et al., Current Protein and Peptide Science, 7:47-56, 2006) and mammalian cells (Wu and Chiang, BioTechniques 21:718-725, 1996). The instant invention takes advantage of the detrimental effect of the overexpression of a functional protein on cell growth, using the ability of an inhibitor of the protein's function to alleviate such detrimental effect, as the means of measuring the activity of a protein inhibitor in intact cells.

The principle of the claimed method is that a compound that inhibits the function of an overexpressed protein will relieve the detrimental effect of such overexpression in a concentration-dependent manner, thereby allowing the determination of the activity of the compound in inhibiting its target protein in live cells.

The invention provides a method for determining the activity of an inhibitor of a target protein that has a deleterious effect on cell growth, the method comprising: providing a first population of cells that overproduces the target protein and a second population of cells that do not overexpress the target protein; determining that the second population of cells grows faster than the first population of cells; treating the first and second populations of cells with different concentrations of an inhibitor of the activity of the target protein; measuring either the growth rate of the first and second populations of cells, or the amount of target protein produced by the first and second populations of cells, or both, determining that the inhibitor causes, in a dose-dependent manner, either an increase in the rate of growth of the first population of cells, or in the amount of target protein produced by the first population of cells, or both, and that the inhibitor does not cause, in a dose-dependent manner, either an increase in the rate of growth of the second population of cells or the amount of target protein produced by the second population of cells; and correlating the concentration of inhibitor with the increase in growth rate of the first population of cells, or in the amount of target protein produced by the first population of cells, or both.

In some embodiments, the first population of cells are recipient cells that overexpress the target protein as a result of being transduced by a first vector that expresses the target protein from an efficient promoter and the second population of cells are recipient cells that are transduced by a second vector that does not express the target protein.

In some embodiments, the first and second populations of cells are a cell line stably transfected by an expression vector comprising a nucleic acid sequence encoding the target protein controlled by an inducible promoter, wherein the first population of cells are grown under conditions that increase transcription from the inducible promoter and the second population of cells are grown under conditions that do not increase transcription from the inducible promoter.

DETAILED DESCRIPTION OF THE PREFERRED EMBODIMENTS

Figure 1:
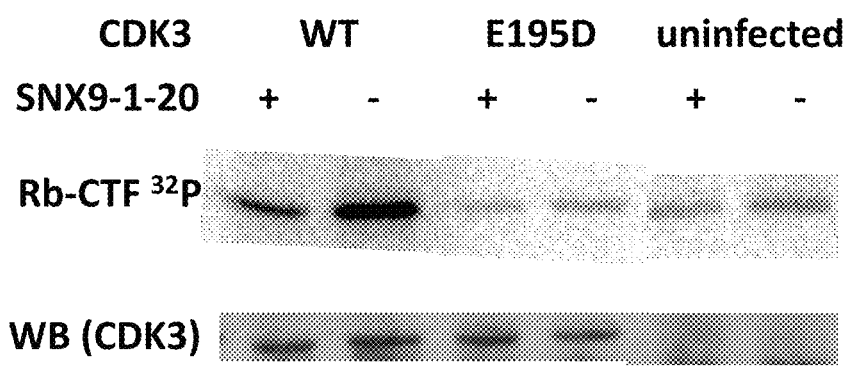
FIG. 1 shows phosphorylated substrate signal for the immunoprecipitate of the HA-tagged wild-type CDK3, mutant E195D CDK3 and untransfected cells, with or without SNX-9-1-20.

The invention provides a method for determining the activity of an inhibitor of a target protein that has a deleterious effect on cell growth. The first step of the method is to determine that the overexpression of the target protein (either the wild-type or an active mutant version, such as mutant oncogenic proteins found in cancer cells) from an expression vector is detrimental to cell growth. Numerous vectors for gene transfer and high-level protein expression in bacterial, yeast, plant or animal cells are known in the art. For relevance to the intended use of the protein inhibitor, the target protein should be expressed in a homologous cellular system, e.g., a bacterial protein in bacterial cells and a mammalian protein in mammalian cells. In some embodiments, a preferred vector for mammalian cells would be a lentiviral or a retroviral vector that can transduce a high fraction of the recipient cells. The vector should express the target protein from an efficient promoter, to maximize the overexpression. The recipient cell line should be selected to allow for a high level of activity of the target protein. For example, if the target protein is a subunit of a multiprotein complex (e.g. a CDK that interacts with cyclins), the recipient cells should express a high level of the other subunit(s) (e.g. a cyclin partner of the target CDK). The detrimental effect of protein overexpression can be evidenced, for example, by finding that the fraction of cells transduced with a vector expressing the wild-type protein is lower than the fraction of cells transduced with the control vector. Such control may be a vector carrying a non-functional mutant form of the same protein, an unrelated physiologically neutral gene (such as, for example, firefly luciferase), or a vector with an insert that expresses no protein or without an insert. The fraction of transduced cells can be established, for example, by scoring the fraction of cells expressing a selectable or observable marker contained in the vector, e.g. cells expressing a fluorescent protein marker can be scored by flow cytometry and cells carrying a drug resistance marker can be scored by the frequency of cells that display resistance to the drug. The detrimental effect of protein overexpression may also be evidenced by a lower expression level of the active protein expressed in the transduced cells relative to a non-functional mutant version of the same protein transduced into the same recipient cells.

The next step of the method is to add the tested inhibitor of the target protein, at several different concentrations, to the cells when they are transduced with a vector expressing the active target protein, to measure the fraction of the cells transduced in the absence of the inhibitor or in the presence of different concentrations of the inhibitor, and to measure a value of the target protein inhibition by the compound (such as the IC50 concentration) based on the concentration-dependent effects of the compound on the increase in the fraction of the transduced cells. In some embodiments, the compound is also added to the cells transduced with a control vector, such as a vector expressing a non-functional mutant protein, to determine that the compound produces either no increase in the fraction of cells transduced with a control vector or a significantly smaller increase than in the cells transduced with a vector expressing the active protein. In an alternative embodiment, the measured value is not the fraction of the transduced cells but the amount of protein expressed by stably transfected cells. Such amount can be determined, for example, by immunoblotting or by an ELISA assay.

In an alternative embodiment, the active target protein is expressed in the cells from an inducible promoter, and the detrimental effect of the protein overexpression is established by the inhibition of the cell growth upon the induction of the promoter.

In some embodiments, the target protein is an enzyme. In some embodiments, the target protein is a kinase. In some embodiments, the target protein is a CDK. In some embodiments, the target protein is CDK3.

Generally, the invention provides a method for determining the activity of an inhibitor of a target protein that has a deleterious effect on cell growth, the method comprising: providing a first population of cells that overexpress the target protein and a second population of cells that do not overexpress the target protein; determining that the second population of cells grows faster than the first population of cells; treating the first and second populations of cells with different concentrations of an inhibitor of the activity of the target protein; measuring either the growth rate of the first and second populations of cells, or the amount of target protein produced by the first and second populations of cells, or both, determining that the inhibitor causes, in a dose-dependent manner, either an increase in the rate of growth of the first population of cells, or in the amount of target protein produced by the first population of cells, or both, and that the inhibitor does not cause, in a dose-dependent manner, either an increase in the rate of growth of the second population of cells or the amount of target protein produced by the second population of cells; and correlating the concentration of inhibitor with the increase in growth rate of the first population of cells, or in the amount of target protein produced by the first population of cells, or both.

In some embodiments, the first population of cells are recipient cells that overexpress the target protein as a result of being transduced by a first vector that expresses the target protein from an efficient promoter and the second population of cells are recipient cells that are transduced by a second vector that does not express the target protein.

In some embodiments, the growth rate of the first and second populations of cells is measured as a fraction of live recipient cells transduced by the vector. In some embodiments, the growth rate of the first and second populations of cells is measured by plating efficiency. In some embodiments, the growth rate of the first and second populations of cells is measured by cell counting. In some embodiments, the growth rate of the first and second populations of cells is measured by the incorporation of a measurable precursor, such as $^3$H-thymidine or bromodeoxyuridine, into DNA.

In some embodiments, the second vector overexpresses a non-functional mutant of the target protein from an efficient promoter.

In some embodiments, the amount of target protein produced by the first and second populations of cells is measured by immunoblotting. In some embodiments, the amount of target protein produced by the first and second populations of cells is measured by ELISA. In some embodiments, the amount of target protein produced by the first and second populations of cells is determined by measuring a biological activity of the target protein.

In some embodiments, the target protein is an enzyme. In some embodiments, the target protein is a cyclin-dependent kinase. In some embodiments, the target protein is cyclin-dependent kinase 3 (CDK3).

In alternative embodiments, the first and second populations of cells are a cell line stably transfected by an expression vector comprising a nucleic acid sequence encoding the target protein controlled by an inducible promoter, wherein the first population of cells are grown under conditions that increase transcription from the inducible promoter and the second population of cells are grown under conditions that do not increase transcription from the inducible promoter.

In some embodiments, the growth rate of the first and second populations of cells is measured by plating efficiency. In some embodiments, the growth rate of the first and second populations of cells is measured by cell counting. In some embodiments, the growth rate of the first and second populations of cells is measured by the incorporation of a measurable precursor, such as $^3$H-thymidine or bromodeoxyuridine, into DNA.

In some embodiments, the amount of target protein produced by the first and second populations of cells is measured by immunoblotting. In some embodiments, the amount of target protein produced by the first and second populations of cells is measured by ELISA. In some embodiments, the amount of target protein produced by the first and second populations of cells is determined by measuring a biological activity of the target protein.

In some embodiments, the target protein is an enzyme. In some embodiments, the target protein is a cyclin-dependent kinase. In some embodiments, the target protein is cyclin-dependent kinase 3 (CDK3).

For purposes of the invention, the following terms have the following meanings.

An "inhibitor of a target protein" means a substance, preferably a small molecule, that reduces at least one biological activity of the target protein.

A "target protein" is the active protein or active mutant thereof, that is being expressed from the expression vector introduced into the cell.

A "protein that has a deleterious effect on cell growth" means a protein that, when overexpressed in the cell, causes the cell to grow more slowly than it would otherwise grow had the protein not been overexpressed in the cell.

A "first population of cells that overexpress the target protein" means a population of cells that expresses the target protein at a higher level from the expression vector than the basal level at which it produces the same protein from its normal chromosomal locus. In some embodiments, the higher level is at least 2-fold. In some embodiments, the higher level is at least 5-fold. In some embodiments, the higher level is at least 10-fold. The first population of cells can be a heterogeneous transiently transfected population of cells or a stably transfected cell line transfected with an inducible promoter.

A "second population of cells that do not overexpress the target protein" means a population of cells that do not produce the target protein, or produce the target protein only at a basal level. In some embodiments the second population of cells overproduces a nonfunctional mutant of the target protein or an unrelated protein.

"Growth rate" means the inverse of the doubling time of the cells, or the transfection efficiency of the cells.

"Dose-dependent manner" means that, within a certain range of concentration of inhibitor, either the growth rate, the amount of target protein produced, or both, is proportional to the concentration of inhibitor.

An "efficient promoter" is a promoter that causes the expression of the target protein, or a nonfunctional mutant thereof at a higher level than it is expressed from the promoter at its native chromosomal locus. In some embodiments, the higher level is at least 2-fold. In some embodiments, the higher level is at least 5-fold. In some embodiments, the higher level is at least 2-fold. In some embodiments, the higher level is at least 10-fold.

A "cell line stably transfected by an expression vector comprising a nucleic acid sequence encoding the target protein controlled by an inducible promoter" is a cell line containing an expression vector from which the target protein is produced under certain growth conditions and not produced, or produced at much lower levels, under certain other growth conditions. In some embodiments, the growth conditions include the presence of a small molecule that induces transcription from the promoter. In some embodiments, the growth conditions include the absence of a small molecule that represses transcription from the promoter.

The following examples are intended to further illustrate certain embodiments of the invention and are not intended to limit its scope.

EXAMPLE 1

Cell-Based Assay for CDK3 Inhibition

Full-length cDNAs of wild-type human CDK3 and of a CDK3 mutant with E195D amino acid substitution, both conjugated with a HA tag, were cloned into a lentiviral vector pHIV-dTomato (AddGene, Cambridge, Mass.). Lentiviral packaging and transduction was carried out as described (Porter et al., Proc. Natl. Acad. Sci. USA 109: 13799-13804, 2012). Lentivirus-containing cell culture supernatant of packaging cells was used to infect MDA-MB-157 breast carcinoma cells, which express a high level of cyclin E (Harwell et al., Cancer Res. 60:481-489, 2000), a binding partner of CDK3. MDA-MB-157 cells were cultured in RPMI with 10% FBS+PS 1x and Glu 1x. Cells infected with lentiviruses expressing wild-type CDK3 or E195D CDK3 mutant, or uninfected cells, were trypsinized and washed with PBS, then lysed with Lysis Buffer II (Pepscan Presto BV, The Netherlands) using twice the volume of the cell pellet. Cell lysates were sonicated at 4°

C., with a Soniprep 150 three times for 6 seconds and stored at −80° C. in aliquots. Prior to immunoprecipitation (IP), the cell extracts were thawed once and centrifuged at 4,000 g for 5 min at 4° C. 50 µg of cell extract was used per IP. Samples were incubated for 1 hr at 4° C. with 0.5 µl of the HA.11 Monoclonal Antibody (Covance, Dedham, MA). After 4 washing steps performed with Lysis buffer II, the IP samples were used for immunoblotting with a CDK3-specific antibody (Santa Cruz SC-826) and for kinase activity assays, as follows.

The kinase substrate (Rb-CTF) and assay kit were from ProQinase (Freiburg, Germany). The kinase assays were done under the conditions described by the manufacturer, using the Km for ATP (determined by the manufacturer for CDK3/Cyclin E1) as the final ATP concentration (6.0 µM). The assays were performed in the presence or in the absence of CDK3 inhibitor SNX9-1-20, at 30 µM concentration, in 25 µl reaction volumes containing 10 µl 2.5× Standard-Assay-Buffer, 5 µl substrate Rb-CTF (stock concentration 0.916 µg/µl), 2.5 µl SNX9-1-20 (300 µM stock in 5% DMSO), 2.5 µl 10× Kinase-Dilution-Buffer, 2.5 µl 120 µM unlabeled ATP and 2.5 µl $^{32}$P-gamma ATP (PerkinElmer, Waltham, Mass.). Reactions were incubated for 40 min at 30° C., then stopped by adding 10 µl 5× Laemlli sample buffer. Each sample was heated to 95° C., centrifuged and analyzed by SDS PAGE in a 1.5 mm thick 10% acrylamide gel, transferred to PVDF membrane, air-dried and exposed in a phosphorimaging device (BioRad Molecular Imager FX®, Hercules, Calif.) to record the radioactive signal. As shown in FIG. 1, the phosphorylated substrate signal for the immunoprecipitate of the wild-type CDK3 was stronger than the background signal of the immunoprecipitate from uninfected cells, and this signal was decreased in the presence of SNX9-1-20, indicating that the wild-type CDK3 expressed in MDA-MB-157 cells is functional. In contrast, the E195D mutant form of CDK3, while detectable in the immunoprecipitates at a similar level by immunoblotting (FIG. 1) did not phosphorylate the substrate beyond the background level, and this assay was not affected by SNX9-1-20 (FIG. 1), indicating that E195D was a nonfunctional kinase mutant of CDK3.

Figure 2:
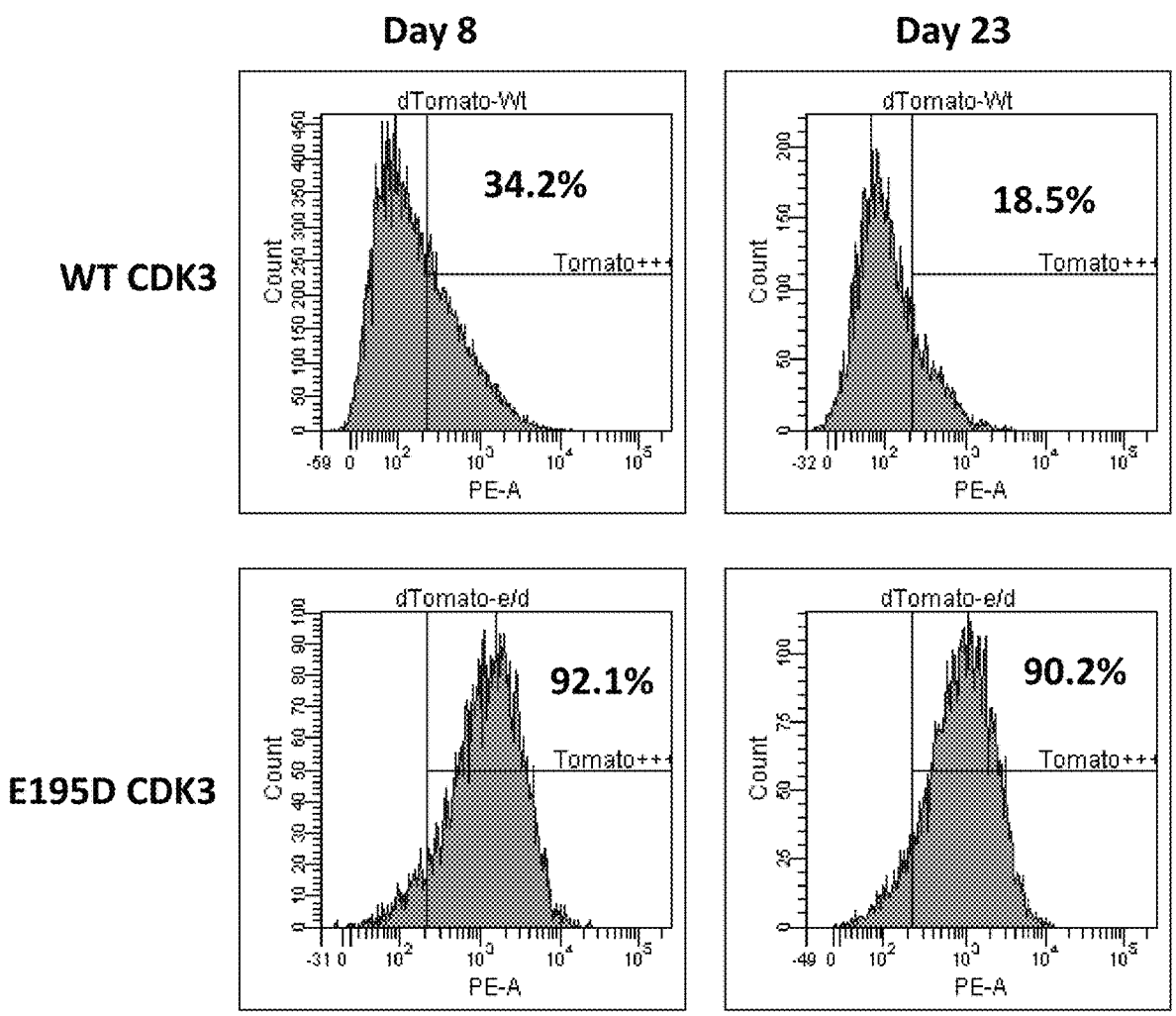
FIG. 2 shows flow profiles of live cells, including the fraction of lentivirus-transduced (Tomato+) cells with the wild-type CDK3 and E195D mutant CDK3 after 8 and 23 days in culture.

The fraction of MDA-MB-157 cells infected with the lentivirus expressing the wild-type CDK3 was significantly lower than the fraction of cells infected with the lentivirus expressing the non-functional mutant E195D. In the experiment shown in FIG. 2, MDA-MB-157 cells were plated at $10^5$ cells per well of a 6-well plate and infected with 1 ml of lentiviral stocks expressing wild-type CDK3 or E195D CDK3 mutant, with 1× polybrene solution. 24 hrs post-infection, the media were changed to virus-free polybrene-free media. 8 days post-infection (FIG. 2) or 23 days post-infection (FIG. 2), the samples were immediately analyzed for Tomato (red fluorescent marker carried in the vector) fluorescence using Becton-Dickinson LSRII flow cytometer. The fraction of the infected cells was defined as the percentage of Tomato+cells. As shown in the flow profiles of live cells in FIG. 2, the fraction of lentivirus-transduced (Tomato+) cells with the wild-type CDK3 was 34.2% in the first assay; this fraction decreased to 18.5% after cell culture growth for 15 days, indicating selection against CDK3-expressing cells. In contrast, the fraction of cells infected with the E195D lentivirus was 92.1% in the first measurement and was essentially unchanged (90.2%) after additional 15-day growth in culture. Hence, the detrimental effect of CDK3 overexpression on MDA-MB-157 cell growth, which limits the infection rate with the CDK3-expressing lentivirus, is dependent on the expression of the functional CDK3 kinase. (In contrast to MDA-MB-157, the resistance to wild-type CDK3 lentivirus infection was not observed in HT1080, 293FT, MDA MB 231 and NIH 3T3 cells, which all express a lower amount of the CDK3's activating partner protein cyclin E.)

Figure 3:
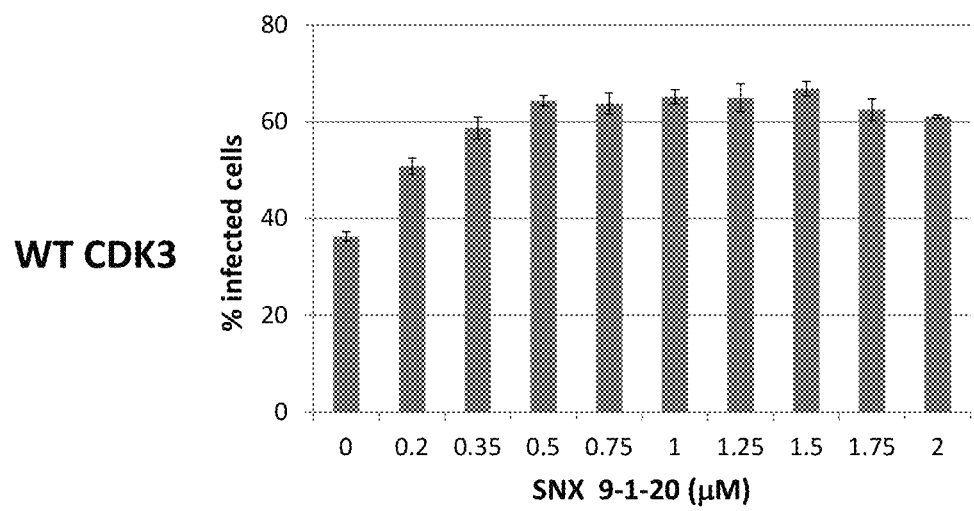
FIG. 3 shows the effects of different concentrations of CDK3 inhibitor SNX9-1-20 on the fraction of MDA-MB-157 cells infected with the wild-type CDK3-expressing lentivirus (FIG. 3a) or E195D mutant CDK3 expressing lentivirus (FIG. 3b).
Figure 3:
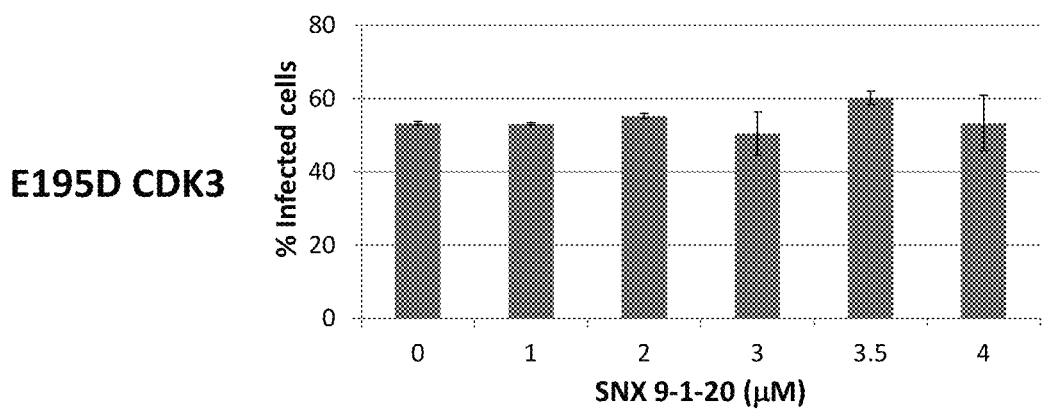

FIG. 3a shows the effects of different concentrations of CDK3 inhibitor SNX9-1-20 on the fraction of MDA-MB-157 cells infected with the wild-type CDK3-expressing lentivirus. In this experiment, MDA-MB-157 cells were plated at $5 \times 10^5$ cells per P100 plate. Cells were infected with 5 ml of media supernatant containing the wild-type CDK3 lentivirus, with 1× polybrene solution. 24 hrs post-infection, the media were changed to virus-free polybrene-free media. 48 hrs post-infection, cells were replated into 24-well plates, at 25,000 cells per well. The culture media (1 ml volume) in each well contained the CDK3 inhibitor SNX9-1-20 at 2, 1.75, 1.5, 1.25, 1, 0.9, 0.75, 0.5, 0.35, 0.2 and 0 µM (DMSO 0.1%), in duplicates. On day 5 after plating, the cells were harvested, centrifuged, suspended in RPMI and aliquoted at 200 µl per well into 96-well plates. 4',6-diamidino-2-phenylindole (DAPI) was added to the final concentration of 1 µg/ml and the samples were analyzed for DAPI and Tomato fluorescence using the flow cytometer. The addition of the CDK3 inhibitor increased the fraction of infected cells from 36.3% in the absence of SNX9-1-20 to 65.15% in the presence of 1 µM SNX9-1-20 (FIG. 3a). In contrast, SNX9-1-20 at 1 µM or higher concentrations had no effect on the fraction of cells infected with the lentivirus expressing E195D non-functional mutant of CDK3 (FIG. 3b), indicating that this effect of the compound was dependent on the CDK3 kinase activity. The increase in the fraction of cells infected with the wild-type CDK3 lentivirus was dependent on the concentration of SNX9-1-20, producing half-maximal effect at a 200 nM concentration of the inhibitor. For comparison, the IC50 for CDK3 kinase inhibition by SNX9-1-20, measured in cell-free assays, was 470-770 nM, depending on the substrate (data not shown). Hence, the increase in the fraction of cells overexpressing functional CDK3 can be used as a target-specific cell-based method to measure the activity of a CDK3 inhibitor.

EXAMPLE 2

Cell-Based Assay for CDK2 Inhibition

Full-length cDNAs of wild-type human CDK2 conjugated with a HA tag, were cloned into a lentiviral vector pHIV-dTomato (AddGene). Lentiviral packaging and transduction was carried out as described (Porter et al., Proc. Natl. Acad. Sci. USA 109: 13799-13804, 2012). Lentivirus-containing cell culture supernatant of packaging cells was used to infect MDA-MB-157 breast carcinoma cells, which express a high level of cyclin E (Harwell et al., Cancer Res. 60:481-489, 2000), a binding partner of CDK2. MDA-MB-157 cells were cultured in RPMI with 10% FBS+PS 1X and Glu 1X.

Figure 4:
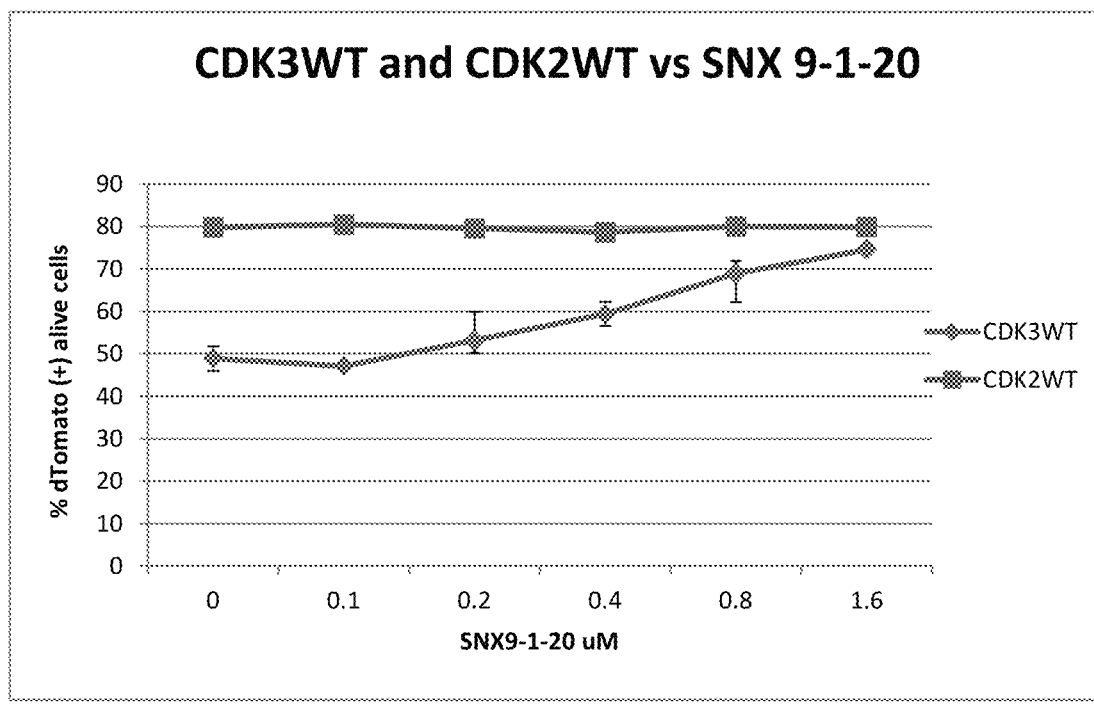
FIG. 4 shows a comparison of the effects of different concentrations of CDK3 inhibitor SNX9-1-20 on the fraction of MDA-MB-157 cells infected with the wild-type CDK3-expressing lentivirus and wild-type CDK2-expressing lentivirus.

FIG. 4 shows a comparison of the effects of different concentrations of CDK3 inhibitor SNX9-1-20 on the fraction of MDA-MB-157 cells infected with the wild-type CDK3-expressing lentivirus and with the wild-type CDK2-expressing lentivirus. In this experiment, MDA-MB-157 cells were plated at $5 \times 10^5$ cells per P100 plate. Cells were infected with 5 ml of media supernatant containing the wild-type of both CDK3 and CDK2 lentivirus, with 1 × polybrene solution. 24 hrs post-infection, the media were changed to virus-free polybrene-free media. 48 hrs post-infection, cells were replated into 24-well plates, at 25,000 cells per well. The culture media (1 ml volume) in each well contained the CDK3 inhibitor SNX9-1-20 at 1.6, 0.8, 0.4, 0.2, 0.1 and 0 μM (DMSO 0.1%), in duplicates. On day 5 after plating, the cells were harvested, centrifuged, suspended in RPMI and aliquoted at 200 μl per well into 96-well plates. 4',6-diamidino-2-phenylindole (DAPI) was added to the final concentration of 1 μg/ml and the samples were analyzed for DAPI and Tomato fluorescence using the flow cytometer. The addition of the CDK3 inhibitor increased the fraction of infected cells from 48.85% in the absence of SNX9-1-20 to 74.55% in the presence of 1.6 μM SNX9-1-20 (FIG. 3a). In contrast, SNX9-1-20 had no effect on the fraction of cells infected with the lentivirus expressing wild-type CDK2, indicating that this effect of the compound was dependent on the CDK3 kinase activity. The increase in the fraction of cells infected with the wild-type CDK3 lentivirus was dependent on the concentration of SNX9-1-20, producing half-maximal effect at a 400 nM concentration of the inhibitor. For comparison, the IC50 for CDK3 kinase inhibition by SNX9-1-20, measured in cell-free assays, was 470-770 nM, depending on the substrate (data not shown). Hence, the increase in the fraction of cells overexpressing functional CDK3 can be used as a target-specific cell-based method to measure the activity of a CDK3 inhibitor.

Figure 5:
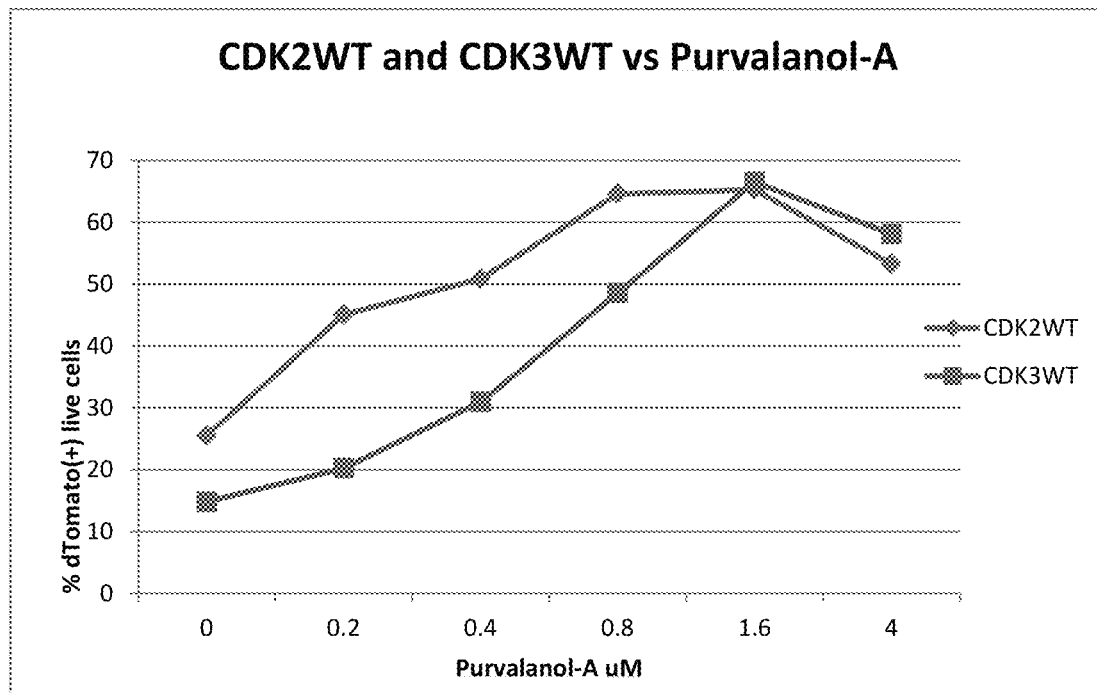
FIG. 5 shows a comparison of the effects of different concentrations of Purvalanol-A on the fraction of MDA-MB-157 cells infected with the wild-type CDK3-expressing lentivirus and wild-type CDK2-expressing lentivirus.

FIG. 5 shows a comparison of the effects of different concentrations of Purvalanol-A on the fraction of MDA-MB-157 cells infected with the wild-type CDK3-expressing lentivirus and with the wild-type CDK2-expressing lentivirus. In this experiment, MDA-MB-157 cells were plated at $5 \times 10^5$ cells per P100 plate. Cells were infected with 5 ml of media supernatant containing the wild-type of both CDK3 and CDK2 lentivirus, with 1 × polybrene solution. 24 hrs post-infection, the media were changed to virus-free polybrene-free media. 48 hrs post-infection, cells were replated into 24-well plates, at 25,000 cells per well. The culture media (1 ml volume) in each well contained the Purvalanol-A at 4, 1.6, 0.8, 0.4, 0.2 and 0 μM (DMSO 0.1%), in duplicates. On day 5 after plating, the cells were harvested, centrifuged, suspended in RPMI and aliquoted at 200 μl per well into 96-well plates. 4',6-diamidino-2-phenylindole (DAPI) was added to the final concentration of 1 μg/ml and the samples were analyzed for DAPI and Tomato fluorescence using the flow cytometer. The addition Purvalanol-A increased the fraction of wild-type CDK3 infected cells from 14.8% in the absence of Purvalanol-A to 66.5% in the presence of 1.6 μM Purvalanol-A. The increase in the fraction of cells infected with the wild-type CDK3 lentivirus was dependent on the concentration of Purvalanol-A, producing half-maximal effect at a 600 nM concentration of the inhibitor. The addition of Purvalanol-A increased the fraction of wild-type CDK2 infected cells from 25.5% in the absence of Purvalanol-A to 65.25% in the presence of 1.6 μM Purvalanol-A. The increase in the fraction of cells infected with the wild-type CDK3 lentivirus was dependent on the concentration of Purvalanol-A, producing half-maximal effect at a 200 nM concentration of the inhibitor.

What is claimed is:

1. A method for determining the activity of an inhibitor of a target protein, wherein the overexpression of the target protein itself has a deleterious effect on cell growth, the method comprising:
   (a) providing a first population of cells that overexpress the target protein and a second population of cells that do not overexpress the target protein;
   (b) determining that the second population of cells grows faster than the first population of cells;
   (c) treating the first and second populations of cells with different concentrations of an inhibitor of the activity of the target protein;
   (d) measuring either the growth rate of the first and second populations of cells, or the amount of target protein produced by the first and second populations of cells, or both,
   (e) determining that the inhibitor causes, in a dose-dependent manner, either an increase in the rate of growth of the first population of cells, or in the amount of target protein produced by the first population of cells, or both, and that the inhibitor does not cause, in a dose-dependent manner, either an increase in the rate of growth of the second population of cells or the amount of target protein produced by the second population of cells; and
   (f) correlating the concentration of inhibitor with the increase in growth rate of the first population of cells, or in the amount of target protein produced by the first population of cells, or both.

2. The method according to claim 1, wherein the first population of cells are recipient cells that overexpress the target protein as a result of being transduced by a first vector that expresses the target protein from an efficient promoter and the second population of cells are recipient cells that are transduced by a second vector that does not express the target protein.

3. The method according to claim 2, wherein the cells are plated after treatment with the inhibitor and growth rate of the first and second populations of cells is measured by plating efficiency.

4. The method according to claim 2, wherein the amount of target protein produced by the first and second populations of cells is measured by immunoblotting.

5. The method according to claim 2, wherein the target protein is an enzyme.

6. The method according to claim 2, wherein the target protein is a cyclin-dependent kinase.

7. The method according to claim 2, wherein the target protein is CDK3.

8. The method according to claim 1, wherein the first and second populations of cells are a cell line stably transfected by an expression vector comprising a nucleic acid sequence encoding the target protein controlled by an inducible promoter, wherein the first population of cells are grown under conditions that increase transcription from the inducible promoter and the second population of cells are grown under conditions that do not increase transcription from the inducible promoter.

9. The method according to claim 8, wherein the cells are plated after treatment with the inhibitor and the growth rate of the first and second populations of cells is measured by plating efficiency.

10. The method according to claim 8, wherein the amount of target protein produced by the first and second populations of cells is measured by immunoblotting.

11. The method according to claim 8, wherein the target protein is an enzyme.

12. The method according to claim 8, wherein the target protein is a cyclin-dependent kinase.

13. The method according to claim 8, wherein the target protein is CDK3.

* * * * *